(12) United States Patent
Okubo

(10) Patent No.: US 8,912,235 B2
(45) Date of Patent: Dec. 16, 2014

(54) OIL-BASED COMPOSITION

(75) Inventor: Koji Okubo, Tokyo (JP)

(73) Assignee: Kao Corporation, Tokyo (JP)

( * ) Notice: Subject to any disclaimer, the term of this patent is extended or adjusted under 35 U.S.C. 154(b) by 39 days.

(21) Appl. No.: 13/519,443

(22) PCT Filed: Dec. 27, 2010

(86) PCT No.: PCT/JP2010/073573
§ 371 (c)(1),
(2), (4) Date: Jun. 27, 2012

(87) PCT Pub. No.: WO2011/081137
PCT Pub. Date: Jul. 7, 2011

(65) Prior Publication Data
US 2012/0295989 A1 Nov. 22, 2012

(30) Foreign Application Priority Data
Dec. 28, 2009 (JP) .................. 2009-298190

(51) Int. Cl.
| | | |
|---|---|---|
| *A61K 8/92* | (2006.01) | |
| *A61Q 19/00* | (2006.01) | |
| *A61K 8/31* | (2006.01) | |
| *A61K 8/33* | (2006.01) | |
| *A61K 8/37* | (2006.01) | |
| *A61K 8/41* | (2006.01) | |
| *A61K 8/81* | (2006.01) | |

(52) U.S. Cl.
CPC . *A61Q 19/00* (2013.01); *A61K 8/31* (2013.01); *A61K 8/33* (2013.01); *A61K 8/37* (2013.01); *A61K 8/375* (2013.01); *A61K 8/41* (2013.01); *A61K 8/8147* (2013.01); *A61K 8/8152* (2013.01); *A61K 8/922* (2013.01); *A61K 2800/10* (2013.01); *A61K 2800/31* (2013.01)
USPC .......................................... 514/772; 524/186

(58) Field of Classification Search
CPC ........... A61K 8/31; A61K 8/33; A61K 8/375; A61K 8/41; A61Q 19/00
USPC ........................................ 514/772.6; 524/186
See application file for complete search history.

(56) References Cited

U.S. PATENT DOCUMENTS

| | | | |
|---|---|---|---|
| 8,178,584 B2 | 5/2012 | Okubo et al. | |
| 2002/0155080 A1* | 10/2002 | Glenn et al. | 424/70.5 |
| 2005/0013839 A1 | 1/2005 | Yamamoto | |
| 2005/0152865 A1 | 7/2005 | Yamamoto et al. | |
| 2011/0263714 A1* | 10/2011 | Okubo | 514/625 |

FOREIGN PATENT DOCUMENTS

| | | |
|---|---|---|
| CN | 1572289 A | 2/2005 |
| CN | 1602181 A | 3/2005 |
| JP | 63 141908 | 6/1988 |
| JP | 63-141908 | 6/1988 |
| JP | 9 169614 | 6/1997 |
| JP | 9-169614 A | 6/1997 |
| JP | 2007-022997 | * 1/2007 |
| JP | 2007 63145 | 3/2007 |
| JP | 2007-63145 A | 3/2007 |
| JP | 2009 62365 | 3/2009 |
| WO | WO2009/019891 | * 2/2009 ........... A61K 31/164 |
| WO | WO 2009/019891 | * 12/2009 ........... A61K 31/164 |

OTHER PUBLICATIONS

Terech et al., Title: Organogels and aerogels of racemic and chiral 12-hydroxyoctadecanoic acid, Langmuir, 1994, 10, 3406-3418, publishedby American Chemical Society.*
Ma et al., Title: Pluronic F127-g-poly(acrylic acid) copolymers as in situ gelling vehicle for ophthalmic drug delivery system, Int J Pharm. Feb. 28, 2008;350(1-2):247-56. Epub Sep. 7, 2007 by Pubmed.gov.*
U.S. Appl. No. 13/536,166, filed Jun. 28, 2012, Okubo.
Terech, P., et al., "Organogels and Aerogels of Racemic and Chiral 12-Hydroxyoctadecanoic Acid," Langmuir, vol. 10, pp. 3406 to 3418, (1994).
Fukasawa, J., et al., "Liquid Crystals of Long-Chain Dialkyl Phosphate Salts in Nonpolar Solvents," Journal of Colloid and Interface Science, vol. 143, No. 1, pp. 69 to 76, (Apr. 1991).

(Continued)

*Primary Examiner* — Johann R Richter
*Assistant Examiner* — Yanzhi Zhang
(74) *Attorney, Agent, or Firm* — Oblon, Spivak, McClelland, Maier & Neustadt, L.L.P.

(57) ABSTRACT

A method for producing a gel-like oily composition including the following components (A), (B), and (C): (A) 4 to 60% by weight of a sphingosine represented by the formula (1) (wherein $R^1$ represents a hydrocarbon group having 4 to 30 carbon atoms; Y represents a methylene group, a methine group, or an oxygen atom; $X^1$, $X^2$, and $X^3$ each represent a hydrogen atom, a hydroxyl group, or an acetoxy group; $X^4$ represents a hydrogen atom, an acetyl group, or a glyceryl group or forms an oxo group together with the adjacent oxygen atom; $R^2$ and $R^3$ each represent a hydrogen atom, a hydroxyl group, a hydroxymethyl group, or an acetoxymethyl group; "R"s each represent a hydrogen atom or an amidino group or represent a hydrocarbon group having a total of 1 to 8 carbon atoms; "a" represents a number of 2 or 3; and a bond represented by a broken line and a solid line indicates a saturated bond or an unsaturated bond); (B) 0.5 to 10% by weight of an anionic polymer having a carboxyl group; and (C) 30 to 95.5% by weight of an oil in a liquid state at 25° C. selected from a hydrocarbon oil, an ester oil, and an ether oil, the method including mixing the components (A), (B), and (C) and heating the resultant mixture to a temperature equal to or more than a melting point of the component (A) to neutralize the component (B) with the component (A) to form a salt.

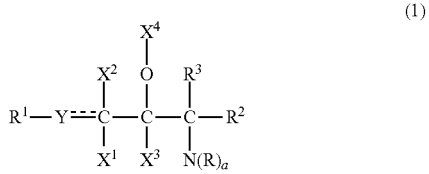

(1)

12 Claims, No Drawings

(56) References Cited

OTHER PUBLICATIONS

Terech, P., et al., "Low Molecular Mass Gelators of Organic Liquids and the Properties of Their Gels," Chem. Rev., vol. 97, pp. 3133 to 3159, (1997).

International Search Report Issued Mar. 29, 2011 in PCT/JP10/073573 Filed Dec. 27, 2010.

Combined Office Action and Search Report issued Mar. 4, 2013 in Chinese Patent Application No. 201080058188.5 with English translation of categories of cited documents.

* cited by examiner

OIL-BASED COMPOSITION

FIELD OF THE INVENTION

The present invention relates to an oily composition.

BACKGROUND OF THE INVENTION

A low molecular weight oil gelling agent has a feature of increasing a viscosity through formation of an intermolecular network in an oil. Oil gelation can be achieved by dispersing the low molecular weight oil gelling agent in the oil under a heating condition, and cooling the resultant dispersion to room temperature (Non Patent Document 1, Non Patent Document 2, and Non Patent Document 3).

However, such gelation results from self-assembly based on intermolecular hydrogen bonds of the gelling agent. Hence, there is a problem in that the resultant gel has a melting point and shows a remarkable reduction in viscosity at a temperature equal to or higher than the melting point.

PRIOR ART DOCUMENT

Non Patent Document

[Non Patent Document 1] Terech, P.; Rodriguez, V.; Barnes, J. D.; McKenna, G. B. Langmuir 1994, 10 3406.
[Non Patent Document 2] Fukasawa, J-I; H. J. Colloid Interface Sci. 1991, 143(1), 69.
[Non Patent Document 3] Terech, P. et al., Chem. Rev. 1997, 97, 3133-3159.

SUMMARY OF THE INVENTION

The present invention provides a method for producing a gel-like oily composition including the following components (A), (B), and (C):
(A) 4 to 60% by weight of a sphingosine represented by the following formula (1):

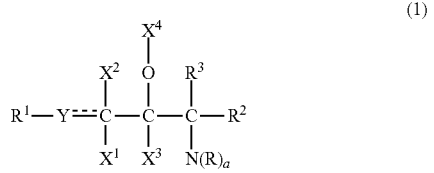

wherein $R^1$ represents a linear, branched, or cyclic, saturated or unsaturated hydrocarbon group having 4 to 30 carbon atoms which is optionally substituted by a hydroxyl group, a carbonyl group, or an amino group; Y represents a methylene group, a methine group, or an oxygen atom; $X^1$, $X^2$, and $X^3$ each independently represent a hydrogen atom, a hydroxyl group, or an acetoxy group, and $X^4$ represents a hydrogen atom, an acetyl group, or a glyceryl group or forms an oxo group together with the adjacent oxygen atom, provided that, when Y represents a methine group, any one of $X^1$ and $X^2$ represents a hydrogen atom and the other is not present, and when $X^4$ forms an oxo group, $X^3$ is not present; $R^2$ and $R^3$ each independently represent a hydrogen atom, a hydroxyl group, a hydroxymethyl group, or an acetoxymethyl group; "R"s each independently represent a hydrogen atom or an amidino group or represent a linear or branched, saturated or unsaturated hydrocarbon group having a total of 1 to 8 carbon atoms which optionally have a substituent selected from the group consisting of a hydroxyl group, a hydroxyalkoxy group, an alkoxy group, and an acetoxy group; "a" represents a number of 2 or 3; and a bond represented by a broken line and a solid line indicates a saturated bond or an unsaturated bond;
(B) 0.5 to 10% by weight of an anionic polymer having a carboxyl group; and
(C) 30 to 95.5% by weight of an oil in a liquid state at 25° C. selected from the group consisting of a hydrocarbon oil, an ester oil, and an ether oil,
the method including mixing the components (A), (B), and (C) and heating the resultant mixture to a temperature equal to or more than a melting point of the component (A) to neutralize the component (B) with the component (A) to form a salt.

The present invention also provides a gel-like oily composition obtained by the method.

EFFECTS OF THE INVENTION

In the oily composition of the present invention, the neutralization of the anionic polymer having a carboxyl group with the sphingosine causes an increase in viscosity based on entanglement of molecules, leading to gelation of a liquid oil. Thus, the oily composition is stable even at high temperature and shows no reduction in viscosity.

EMBODIMENTS FOR CARRYING OUT THE INVENTION

The present invention relates to an oil gelling agent and an oily gel composition which show no reduction in viscosity even at high temperature after gel formation.

The inventors of the present invention have found that gelation of an oil can be achieved by neutralizing an anionic polymer having a carboxyl group with a sphingosine, thereby producing an oily composition stable even at high temperature.

The sphingosine as a component (A) to be used in the present invention is represented by the formula (1).

In the formula, $R^1$ represents a linear, branched, or cyclic, saturated or unsaturated hydrocarbon group having 4 to 30 carbon atoms which is optionally substituted by a hydroxyl group, a carbonyl group, or an amino group, preferably having 7 to 22 carbon atoms which is optionally substituted by a hydroxyl group. Of those, preferred are a linear or branched alkyl group having 10 to 20 carbon atoms, and a linear or branched alkyl group having 10 to 20 carbon atoms and having a hydroxyl group at the end on the Y side, provided that, in the case of the branched alkyl group, the group is methyl branched, for example. Specifically, preferred are a tridecyl group, a tetradecyl group, a pentadecyl group, a hexadecyl group, a 1-hydroxytridecyl group, a 1-hydroxypentadecyl group, an isohexadecyl group, and an isostearyl group.

Y represents any one of a methylene group ($CH_2$), a methine group (CH), and an oxygen atom.

$X^1$, $X^2$, and $X^3$ each independently represent a hydrogen atom, a hydroxyl group, or an acetoxy group, $X^4$ represents a hydrogen atom, an acetyl group, a glyceryl group, or a substituent that forms an oxo group together with the adjacent oxygen atom. A case where none or one of $X^1$, $X^2$, and $X^3$ represents a hydroxyl group, the others each represent a hydrogen atom, and $X^4$ represents a hydrogen atom is preferred. It should be noted that, when Y represents a methine group, any one of $X^1$ and $X^2$ represents a hydrogen atom and the other is not present. Further, when $X^4$ forms an oxo group, $X^3$ is not present.

$R^2$ and $R^3$ each independently represent a hydrogen atom, a hydroxyl group, a hydroxymethyl group, or an acetoxymethyl group, and $R^3$ preferably represents a hydrogen atom.

Further, "a" represents a number of 2 or 3. When "a" represents 2, "R"s each independently represent $R^4$ and $R^5$, and when "a" represents 3, "R"s each independently represent $R^4$, $R^5$, and $R^6$.

$R^4$, $R^5$, and $R^6$ each independently represent a hydrogen atom or an amidino group or represent a linear or branched, saturated or unsaturated hydrocarbon group having a total of 1 to 8 carbon atoms which optionally have a substituent selected from the group consisting of a hydroxyl group, a hydroxyalkoxy group, an alkoxy group, and an acetoxy group. Here, the hydroxyalkoxy group by which the hydrocarbon group is optionally substituted is preferably a linear or branched hydroxyalkoxy group having 1 to 7 carbon atoms. Further, the alkoxy group is preferably a linear or branched alkoxy group having 1 to 7 carbon atoms. $R^4$, $R^5$, and $R^6$ each represent, for example: a hydrogen atom; a linear or branched alkyl group such as methyl, ethyl, propyl, 2-ethylhexyl, or isopropyl; an alkenyl group such as vinyl or allyl; an amidino group; or a hydrocarbon group having a total of 1 to 8 carbon atoms substituted by one to six groups selected from the group consisting of a hydroxyl group, a hydroxyalkoxy group, and an alkoxy group, such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl, or 1,1-bis(hydroxymethyl)-2-hydroxyethyl.

Of those, preferred example of $R^4$, $R^5$ and $R^6$ includes a hydrogen atom, a methyl group, or an alkyl group which is optionally substituted by one to three substituents selected from the group consisting of a hydroxyl group and a hydroxyalkoxy group, such as 2-hydroxyethyl, 1,1-dimethyl-2-hydroxyethyl, 1,1-bis(hydroxymethyl)ethyl, or 2-(2-hydroxyethoxy)ethyl.

The sphingosine represented by the formula (1) is preferably a natural or natural type sphingosine represented by the following formula (2) and a derivative thereof (hereinafter, referred to as natural type sphingosine) or a pseudo type sphingosine having a sphingosine structure represented by the following formula (3) (hereinafter, referred to as pseudo type sphingosine).

(I) A natural type sphingosine represented by the formula (2).

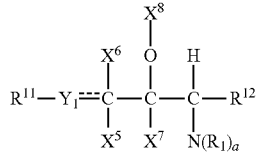

(2)

(In the formula: $R^{11}$ represents a linear, branched, or cyclic, saturated or unsaturated hydrocarbon group having 7 to 19 carbon atoms which is optionally substituted by a hydroxyl group; $Y_1$ represents a methylene group or a methine group; $X^5$, $X^6$, and $X^7$ each independently represent a hydrogen atom, a hydroxyl group, or an acetoxy group, and $X^8$ represents a hydrogen atom or forms an oxo group together with the adjacent oxygen atom (provided that, when $Y_1$ represents a methine group, any one of $X^5$ and $X^6$ represents a hydrogen atom and the other is not present, and when $X^8$ forms an oxo group, $X^7$ is not present); $R^{12}$ represents a hydroxymethyl group or an acetoxymethyl group; "$R_1$"s each independently represent a hydrogen atom or an amidino group or represent a linear or branched, saturated or unsaturated hydrocarbon group having a total of 1 to 4 carbon atoms which optionally have a substituent selected from the group consisting of a hydroxyl group, a hydroxyalkoxy group, an alkoxy group, and an acetoxy group; "a" represents a number of 2 or 3; and a bond represented by a broken line and a solid line indicates a saturated bond or an unsaturated bond.)

Here, $R^{11}$ preferably represents a linear, branched, or cyclic, saturated or unsaturated hydrocarbon group having 7 to 19 carbon atoms, more preferably represents a linear, saturated or unsaturated hydrocarbon group having 13 to 15 carbon atoms. "a" preferably represents 2, "$R_1$"s preferably each independently represent a hydrogen atom or a linear or branched alkyl group having 1 to 4 carbon atoms.

Specific examples of the natural type sphingosine represented by the formula (2) include a natural sphingosine, dihydrosphingosine, phytosphingosine, sphingadienine, dehydrosphingosine, dehydrophytosphingosine, and N-alkyl forms (such as N-methyl forms) thereof.

As those sphingosines, there may be used an optically active isomer of a natural type (D(+) isomer) or an optically active isomer of a non-natural type (L(−) isomer). Alternatively, there may be used a mixture of the natural type and the non-natural type. A relative configuration of each of the compounds may be a configuration of a natural type or a configuration of a non-natural type other than the natural type, or may be a configuration of a mixture thereof.

In addition, preferred are PHYTOSPHINGOSINE (INCI name; 8th Edition) and sphingosines represented by the following formulae.

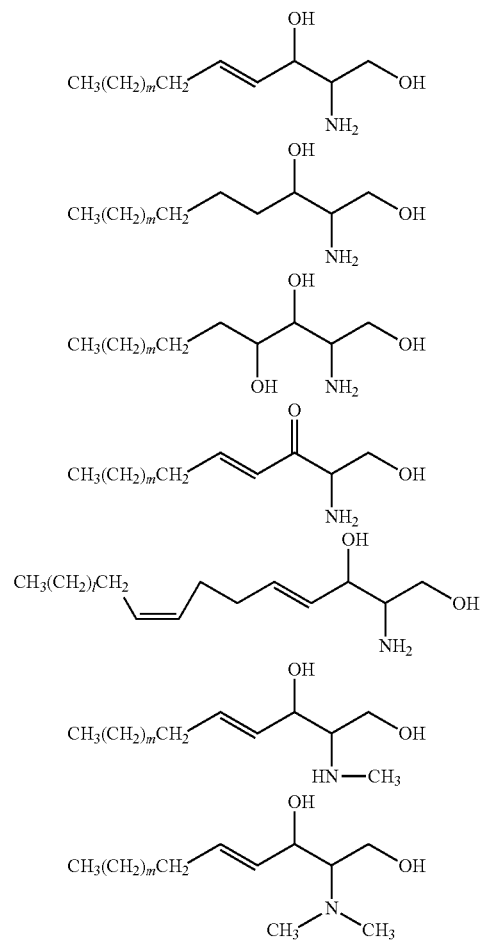

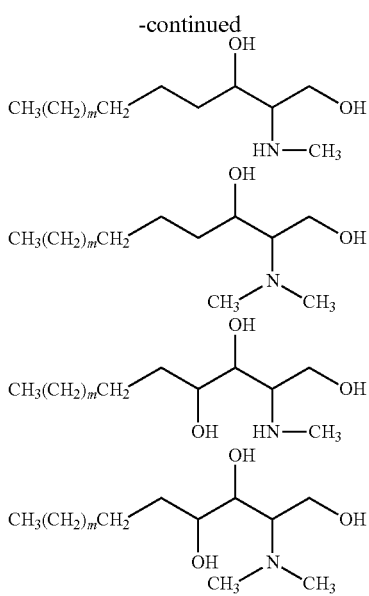

(In the formulae: m represents 5 to 17; and l represents 1 to 13.)

Those sphingosines may be any of extracts from natural products and synthetic products, and commerically available products may be used.

Examples of the commercially available products of the natural type sphingosine include D-Sphingosine (4-Sphingenine) (SIGMA-ALDRICH), DS-phytosphingosine (DOOSAN), and phytosphingosine (COSMOFERM).

(II) A pseudo type sphingosine represented by the formula (3).

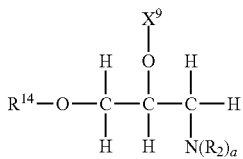

(3)

(In the formula: $R^{14}$ represents a linear, branched, or cyclic, saturated or unsaturated hydrocarbon group having 10 to 22 carbon atoms which is optionally substituted by a hydroxyl group; $X^9$ represents a hydrogen atom, an acetyl group, or a glyceryl group; and "$R_2$" each independently represent a hydrogen atom or an amidino group or represent a linear or branched, saturated or unsaturated hydrocarbon group having a total of 1 to 8 carbon atoms which optionally have a substituent selected from the group consisting of a hydroxyl group, a hydroxyalkoxy group, an alkoxy group, and an acetoxy group, and "a" represents a number of 2 or 3.)

Here, $R^{14}$ preferably represents an iso-branched alkyl group having 14 to 20 carbon atoms, more preferably represents an isostearyl group. The isostearyl group is most preferably an isostearyl group obtained by using, as a raw material oil, isostearyl alcohol derived from a byproduct in the manufacture of a dimer acid using a fatty acid derived from an animal or vegetable oil.

Further, when "a" represents 2, "$R_2$"s each independently represent $R^{15}$ and $R^{16}$, and when "a" represents 3, "$R_2$"s each independently represent $R^{15}$, $R^{16}$, and $R^{17}$.

$R^{15}$, $R^{16}$, and $R^{17}$ each represent, for example: a hydrogen atom; a linear or branched alkyl group such as methyl, ethyl, propyl, 2-ethylhexyl, or isopropyl; an alkenyl group such as vinyl or allyl; an amidino group; or an alkyl group having a total of 1 to 8 carbon atoms and having a substituent selected from the group consisting of a hydroxyl group, a hydroxyalkoxy group, and an alkoxy group, such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl, or 1,1-bis(hydroxymethyl)-2-hydroxyethyl.

Of those, preferred is a secondary amine in which any one of $R^{15}$ and $R^{16}$ represents a hydrogen atom and the other represents 2-hydroxyethyl, 1,1-dimethyl-2-hydroxyethyl, 1,1-bis(hydroxymethyl)ethyl, or 2-(2-hydroxyethoxy)ethyl.

As the pseudo type sphingosine, preferred is one in which $R^{14}$ represents an isostearyl group, $X^9$ represents a hydrogen atom, $R^{15}$ represents a hydrogen atom, $R^{16}$ represents an alkyl group substituted by one to three substituents selected from the group consisting of a hydroxyl group and a hydroxyalkoxy group, such as a 2-hydroxyethyl group, a 1,1-bis(hydroxymethyl)ethyl group, a 1,1-dimethyl-2-hydroxyethyl group, or a 2-(2-hydroxyethoxy)ethyl group.

Specific examples of the pseudo type sphingosine include the following pseudo type sphingosines (i) to (iv).

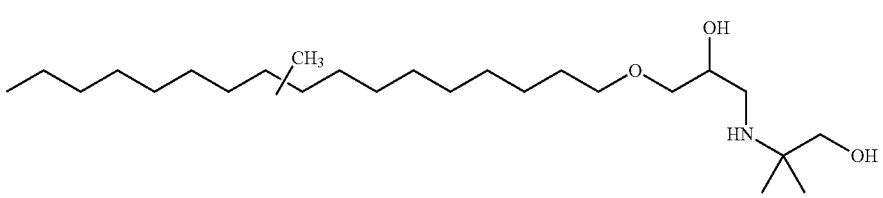

(i)

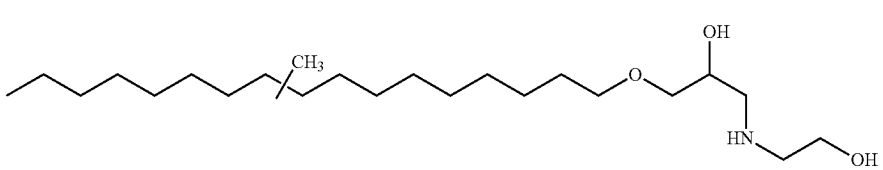

(ii)

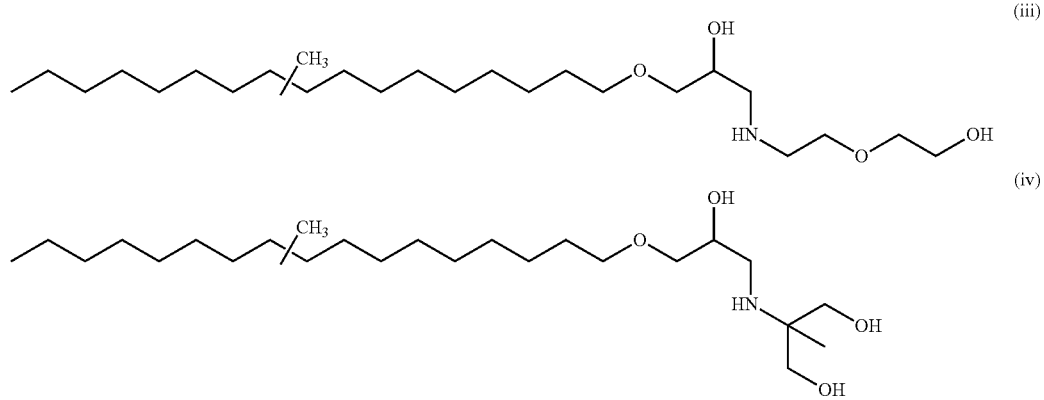

Of those, a pseudo type sphingosine (ii) is preferred.

One or more kinds of component (A) may be used. The component is contained at 4 to 60% by weight, preferably 9 to 30% by weight in the composition of the present invention from the viewpoint of completely neutralizing a polymer to form a salt.

A component (B) to be used in the present invention is an anionic polymer having a carboxyl group, preferably a polymer obtained by polymerization of a monomer having a carboxyl group such as acrylic acid or methacrylic acid. Alternatively, the component (B) may be a polymer obtained by copolymerization of a monomer such as acrylic acid or methacrylic acid with any other hydrophobic monomer having a polymerizable group such as an unsaturated bond, and may contain a cross-linking agent.

The component (B) is preferably an anionic polymer including acrylic acid or methacrylic acid as a monomer.

More specifically, there are given, for example, polyacrylic acid, polymethacrylic acid, an acrylic acid-alkyl methacrylate copolymer, an acrylates/C10-30 alkyl acrylate crosspolymer, a carboxyvinyl polymer (carbomer), and (meth)acrylic acid/C10-30 alkyl(meth)acrylate/polyoxyethylene C10-30 alkyl ether(meth)acrylate.

Of those polymers, polyacrylic acid, polymethacrylic acid, an acrylic acid-alkyl methacrylate copolymer, an acrylates/C10-30 alkyl acrylate crosspolymer, and a carboxyvinyl polymer (carbomer) are preferred from the viewpoint of handleability.

As those polymers, there may be used commercially available products such as ACULYN 88, ACULYN 22, ACULYN 28, and ACULYN 38 (all of which are manufactured by Rohm and Haas Company) and Carbopol 980, Carbopol 981, Carbopol Ultrez 10, Carbopol Ultrez 20, Carbopol Ultrez 21, Carbopol ETD2020, Carbopol AQUA-SF1, PEMULEN TR-1, and PEMULEN TR-2 (all of which are manufactured by Lubrizol Advanced Materials, Inc.).

The anionic polymer as the component (B) has a weight average molecular weight of preferably 100,000 or more, more preferably 1,000,000 or more, and the weight average molecular weight is preferably 10,000,000 or less from the viewpoint of providing good handleability and a sufficient effect of increasing a viscosity.

One or more of component (B) may be used. The component (B) is contained at 0.5 to 10% by weight, preferably 1 to 7% by weight in the composition of the present invention. The use of the component at a content within this range provides a sufficient effect of increasing a viscosity. The content of the component (B) may be adjusted to produce gels depending on purposes, such as an oil gel with a fresh appearance and a rigid gel.

In the present invention, the weight ratio (A)/(B) of the component (A) to the component (B) is preferably 5 to 30, more preferably 5 to 12 from the viewpoint of providing a sufficient effect of increasing a viscosity.

A component (C) to be used in the present invention is an oil in a liquid state at 25° C. selected from the group consisting of a hydrocarbon oil, an ester oil, and an ether oil.

Specific examples thereof include: hydrocarbon oils such as liquid paraffin, liquid isoparaffin, hydrogenated polyisobutene, squalane, n-octane, n-heptane, and cyclohexane; ester oils such as diisostearyl malate, octyldodecyl lactate, isotridecyl isononanoate, octyldodecyl myristate, isopropyl palmitate, isopropyl isostearate, butyl stearate, myristyl myristate, isopropyl myristate, octyldodecyl myristate, di-2-ethylhexyl adipate, diisopropyl sebacate, neopentyl glycol dicaprate, tricaproin, pentaerythrityl 2-ethylhexanoate, meadowfoam oil, and olive oil; and ether oils such as cetyl isobutyl ether, dioctyl ether, ethylene glycol monolauryl ether, ethylene glycol dioctyl ether, and glycerol monooleyl ether. It should be noted that those oils each have a viscosity at 25° C. of 0.5 to 500 mPa·s.

Of those, from the viewpoint of easily increasing a viscosity, preferred are: hydrocarbon oils such as liquid paraffin, liquid isoparaffin, hydrogenated polyisobutene, squalane, n-octane, n-heptane, and cyclohexane; and ether oils such as cetyl isobutyl ether, dioctyl ether, ethylene glycol monolauryl ether, ethylene glycol dioctyl ether, and glycerol monooleyl ether.

One or more kinds of component (C) may be used. The component is contained at 30 to 95.5% by weight, preferably 70 to 90.5% by weight in the composition of the present invention. A content within this range is preferred from the viewpoint of providing an optimum effect of increasing a viscosity.

The oily composition of the present invention may be produced by mixing the components (A), (B), and (C) and heating the resultant mixture to a temperature equal to or more than a melting point of the component (A) to neutralize the component (B) with the component (A) to form a salt.

Further, a gel-like oily composition may be produced by mixing the components (A) and (B), heating the mixture to a temperature equal to or more than a melting point of the component (A) to neutralize the component (B) with the component (A) to form a salt, and then mixing the salt with the component (C).

In addition, a gel-like oily composition may be produced by melting the component (A) by heating to a temperature equal to or more than a melting point of the component (A), mixing and dissolving the melt in the component (C) heated to a temperature equal to or more than the melting point of the component (A), and then adding the component (B) to the solution to neutralize the component (A) to form a salt.

The thus obtained oil gel may be cooled to room temperature (25° C.) by being left to stand at room temperature (25° C.) or by being forcibly cooled using a cooling medium such as water. It should be noted that, in the step of mixing the components (A) and (B) to form a salt, it is preferred that 0.5% by weight or less of water be contained, and it is more preferred that no water be contained.

In the present invention, the anionic polymer having a carboxyl group as the component (B) is generally water-soluble and oil-insoluble. However, when the component is mixed with the sphingosine as the component (A) and the mixture is dissolved with heating, the component (B) is neutralized with the component (A) to form a salt of the component (B) with the component (A). The salt functions as an oil gelling agent. The component (B) neutralized with the component (A) has an increased affinity to the component (C) and can be easily dissolved in the component (C). As a result, an increase in viscosity of an oil can be achieved. The thus obtained gel has no particular melting point and shows small reduction in viscosity even at high temperature.

The oily composition of the present invention is a gel-like composition in which an oil phase including the component (C) is a continuous phase. The oily composition has a viscosity at 20° C. of preferably 1,000 to $10^{12}$ mPa·s, more preferably 10,000 to $10^{12}$ mPa·s. Further, the viscosity is preferably 10,000 Pa·s or less from the viewpoint of good handleability. The viscosity is measured with a helical viscometer to be described later.

The oily composition of the present invention is applicable as a cosmetic, an ointment, a coating liquid, a paint, or the like.

When the oily composition is applied as a cosmetic, the oily composition may contain, in addition to the above-mentioned components, components generally used in a cosmetic, such as a surfactant, an alcohol, a polyol, a polymeric compound, a UV absorber, an antioxidant, a dye, a perfume, a pigment, an antifouling agent, a humectant, and the like, and is applicable as an oily cosmetic to be used for skin, lips, eyelashes, nails, or hair. For example, the oily composition is applicable as lip cosmetics such as lip sick, lip gloss, and lip liner, makeup cosmetics such as mascara, eye liner, eye shadow, cheek color, foundation, and concealer, cream, milky lotion, beauty lotion, massage agent, deodorant, sunscreen, hair growing agent, hair colorant, hair wax, and hair foam.

Further, in the present invention, a compound obtained by neutralizing the anionic polymer having a carboxyl group as the component (B) with the sphingosine (1) as the component (A) may be used as an oil gelling agent. As described above, the anionic polymer may be neutralized to form a salt by mixing the anionic polymer and the sphingosine, and heating the mixture to a temperature equal to or more than a melting point of the sphingosine. The salt can be easily dissolved to show a viscosity when being mixed with a hydrocarbon oil, an ester oil, an ether oil, or the like and heated, and can have a sufficient viscosity even after having been cooled to room temperature.

In the oily composition of the present invention, it is more preferred to use a combination of preferred ranges of each component and each production method.

EXAMPLES

Examples 1 to 11 and Comparative Examples 1 to 4

Oily compositions having the compositions shown in Table 1 and Table 2 were each produced and evaluated for its gel viscosity and gel stability. Table 1 and Table 2 show the results collectively.

(Production Method)

(1) Examples 1 to 6

The component (A) and the component (C) were mixed and homogenized by stirring. After that, the component (B) was added and homogeneously dispersed. The resultant mixture was then heated to a temperature (90° C.) equal to or more than a melting point of the component (A). After the confirmation of the dissolution of the component (B), the solution was cooled to room temperature to afford an oily composition.

(2) Examples 7 to 11

The component (A) was melted by being heated to a temperature (90° C.) equal to or more than its melting point, and mixed and dissolved in the component (C) heated to 90° C. After that, the component (B) was added. After it was confirmed that the component (B) was dissolved to form a homogeneous solution, the solution was cooled to room temperature to afford an oily composition.

(3) Comparative Examples

The component (A) was melted by being heated to a temperature (90° C.) equal to or more than its melting point, and mixed and homogeneously dissolved or dispersed in the component (C) or silicone oil heated to 90° C. After that, the component (B) or a polymer was added, and the mixture was homogenized by thoroughly stirring and then cooled to room temperature to afford an oily composition.

In Comparative Example 4, dextrin palmitate was added to the component (C), and the mixture was heated to 70° C., homogenized by thoroughly stirring, and then cooled to room temperature to afford an oily composition.

(Evaluation method)

(1) Gel Viscosity:

The viscosity at 20° C. or 60° C. of each composition was measured using a B8R type helical viscometer (Toki Sangyo Co., Ltd.) with a T-F rotor at a rotation number of 12 rpm for 1 minute.

(2) Gel Stability:

Each composition was stored at 20° C. for 1 month and then visually observed and evaluated for its appearance based on the following criteria.

1; No change was observed in gel properties.

2; Separation was observed in a gel.

3; Discoloration was observed in a gel.

TABLE 1

| | Component (% by weight) | Example 1 | Example 2 | Example 3 | Example 4 | Example 5 | Example 6 | Example 7 |
|---|---|---|---|---|---|---|---|---|
| A | Hydroxyethylisostearyloxyisopropanolamine | 8.5 | | 27 | | | 29 | 60 |
| A | Hydroxyethylstearyloxyisopropanolamine | | 18 | | | | | |
| A | Phytosphingosine | | | | 24 | | | |
| A | Sphingosine | | | | | 27 | | |
| | Oleylamine | | | | | | | |
| B | Carbomer (Carbopol 981, Lubrizol Advanced Materials, Inc.; molecular weight: 1,250,000) | | 2 | | | | | |
| B | Carbomer (Carbopol 980, Lubrizol Advanced Materials, Inc.; molecular weight: 4,000,000) | | | | 4 | | | |
| B | (Acrylates/C10-30 alkyl acrylate) crosspolymer (Carbopol ETD2020, Lubrizol Advanced Materials, Inc.; molecular weight: about 3,000,000) | | | | | 3 | | |
| B | Carbomer (Carbopol ULTREZ 10, Lubrizol Advanced Materials, Inc.) | | | | | | | 10 |
| B | Carbomer (Carbopol ULTREZ 20, Lubrizol Advanced Materials, Inc.) | | | 3 | | | | |
| B | Carbomer (Carbopol ULTREZ 21, Lubrizol Advanced Materials, Inc.) | | | | | | 1 | |
| B | Acrylates copolymer (Carbopol AQUA-SF1, Lubrizol Advanced Materials, Inc.) | | | | | | | |
| B | (Alkyl acrylate/steareth-20 methacrylate) copolymer (ACULYN 22 manufactured by Rohm and Haas Company) | | | | | | | |
| B | (Acrylic acid/C10-30 alkyl acrylate) crosspolymer (Pemulen TR-1, Lubrizol Advanced Materials, Inc.; molecular weight: about 1,500,000) | 1.5 | | | | | | |
| B | (Acrylic acid/C10-30 alkyl acrylate) crosspolymer (Pemulen TR-2, Lubrizol Advanced Materials, Inc.; molecular weight: about 1,000,000) | | | | | | | |
| | Sodium stearoxy PG hydroxyethylcellulose sulfonate | | | | | | | |
| C | Liquid isoparaffin | Balance | | | | | Balance | |
| C | Cetyl isobutyl ether (ASE 166 manufactured by Kao Corporation) | | | | | | | |
| C | Isotridecyl isononanoate (SALACOS 913 manufactured by The Nisshin OilliO Group, Ltd.) | | Balance | | | | | Balance |
| C | Olive oil (CROPURE OL manufactured by Croda Japan K.K.) | | | | Balance | Balance | | |
| C | Neopentyl glycol dicaprate (ESTEMOL N01 manufactured by The Nisshin OilliO Group, Ltd.) | | | Balance | | | | |
| | Silicone 6 cs | | | | | | | |
| | Total | 100 | 100 | 100 | 100 | 100 | 100 | 100 |
| | Gel viscosity (20° C.) (mPa·s) | 88,000 | 184,000 | 900,000 | 5,320,000 | 900,000 | 27,150 | $1.5 \times 10^{11}$ |
| | Gel viscosity (60° C.) (mPa·s) | 87,000 | 182,000 | 896,000 | 5,310,000 | 895,000 | 26,800 | $1.5 \times 10^{11}$ |
| | Gel stability | 1 | 1 | 1 | 1 | 1 | 1 | 1 |
| | A/B | 5.67 | 9 | 9 | 6 | 9 | 29 | 6 |

TABLE 2

| | Component (% by weight) | Example 8 | Example 9 | Example 10 | Example 11 | Comparative Example 1 | Comparative Example 2 | Comparative Example 3 | Comparative Example 4 |
|---|---|---|---|---|---|---|---|---|---|
| A | Hydroxyethylisostearyloxyisopropanolamine | | | | | 9 | | | |
| A | Hydroxyethylstearyloxyisopropanolamine | 18 | | | | | 9 | | |
| A | Phytosphingosine | | 18 | | 9 | | | | |
| A | Sphingosine | | | 25 | | | | | |
| | Oleylamine | | | | | | | | 9 |
| B | Carbomer (Carbopol 981, Lubrizol Advanced Materials, Inc.; molecular weight: 1,250,000) | | | | 0.5 | | | | |
| B | Carbomer (Carbopol 980, Lubrizol Advanced Materials, Inc.; molecular weight: 4,000,000) | | | | | | | | |
| B | (Acrylates/C10-30 alkyl acrylate) crosspolymer (Carbopol ETD2020, Lubrizol Advanced Materials, Inc.; molecular weight: about 3,000,000) | | | | | | | 1 | |
| B | Carbomer (Carbopol ULTREZ 10, Lubrizol Advanced Materials, Inc.) | | | | | | | | |
| B | Carbomer (Carbopol ULTREZ 20, Lubrizol Advanced Materials, Inc.) | | | | | | | | |
| B | Carbomer (Carbopol ULTREZ 21, Lubrizol Advanced Materials, Inc.) | | | | | | | | |

TABLE 2-continued

| Component (% by weight) | | Example 8 | Example 9 | Example 10 | Example 11 | Comparative Example 1 | Comparative Example 2 | Comparative Example 3 | Comparative Example 4 |
|---|---|---|---|---|---|---|---|---|---|
| B | Acrylates copolymer (Carbopol AQUA-SF1, Lubrizol Advanced Materials, Inc.) | 5 | | | | | | | |
| B | (Alkyl acrylate/steareth-20 methacrylate) copolymer (ACULYN 22 manufactured by Rohm and Haas Company) | | 6.7 | | | | | | |
| B | (Acrylic acid/C10-30 alkyl acrylate) crosspolymer(Pemulen TR-1, Lubrizol Advanced Materials, Inc.; molecular weight: about 1,500,000) | | | | | | 1 | | |
| B | (Acrylic acid/C10-30 alkyl acrylate) crosspolymer (Pemulen TR-2, Lubrizol Advanced Materials, Inc.; molecular weight: about 1,000,000) | | | 1 | | | | | |
| | Dextrin palmitate (Rheopearl KL, Chiba Flour Milling Co., Ltd.) | | | | | | | | 10 |
| | Sodium stearoxy PG hydroxyethylcellulose sulfonate | | | | | 1 | | | |
| C | Liquid isoparaffin | | | | | Balance | | | Balance |
| C | Cetyl isobutyl ether (ASE 166 manufactured by Kao Corporation) | Balance | | Balance | Balance | | | | |
| C | Isotridecyl isononanoate (SALACOS 913 manufactured by The Nisshin OilliO Group, Ltd.) | | | | | | | Balance | |
| C | Olive oil (CROPURE OL manufactured by Croda Japan K.K.) | | | | | | | | |
| C | Neopentyl glycol dicaprate (ESTEMOL N01 manufactured by The Nisshin OilliO Group, Ltd.) | | Balance | | | | | | |
| | Silicone 6 cs | | | | | | | | |
| Total | | 100 | 100 | 100 | 100 | 100 | 100 | 100 | 100 |
| Gel viscosity (20° C.) (mPa · s) | | 88,000 | 184,000 | 22,050 | 1,440 | 560 | 30 | 400 | 140,000 |
| Gel viscosity (60° C.) (mPa · s) | | 87,000 | 181,000 | 21,000 | 1,400 | 560 | 30 | 400 | 450 |
| Gel stability | | 1 | 1 | 1 | 1 | — | — | — | 1 |
| A/B | | 12 | 9 | 25 | 18 | 9 | 9 | 9 | — |

Examples 12 to 14

Oily compositions having the compositions shown in Table 3 were each produced and evaluated for its gel viscosity and gel stability in the same manner as in Examples 1 to 11. Table 3 shows the results collectively.

(Production Method)

The components (A) and (B) were mixed and heated to a temperature (90° C.) equal to or more than a melting point of the component (A) to neutralize the component (B) with the component (A), followed by addition of the component (C). After it was confirmed that the mixture was dissolved to be a homogeneous solution, the solution was cooled to room temperature to afford an oily composition.

TABLE 3

| | Component (% by weight) | Example 12 | Example 13 | Example 14 |
|---|---|---|---|---|
| A | Hydroxyethylisostearyloxy-isopropanolamine | 4 | 15 | 30 |
| B | Carbomer (Carbopol 980, Lubrizol Advanced Materials, Inc.; molecular weight: 4,000,000) | 0.8 | | |
| B | Carbomer (Carbopol ULTREZ 21, Lubrizol Advanced Materials, Inc.) | | 0.5 | 1 |
| C | Liquid isoparaffin | Balance | Balance | Balance |
| Total | | 100 | 100 | 100 |
| Gel viscosity (20° C.) (mPa · s) | | 18,400 | 13,200 | 28,500 |
| Gel stability | | 1 | 1 | 1 |
| A/B | | 5 | 30 | 30 |

Example 15

Moisturizing Oil Gel

A moisturizing oil gel having the composition shown below was produced.

The resultant oil gel has a fresh transparent appearance and can provide a high moisturizing effect through its application to skin. Further, the oil gel is stable even at high temperature and shows no reduction in viscosity.

(Components)

| | |
|---|---|
| (1) Squalane | 40.0 (% by weight) |
| (2) Liquid isoparaffin | 50.0 |
| (3) Phytosphingosine | 0.1 |
| (4) Hydroxyethylisostearyloxyisopropanolamine | 8.9 |
| (5) Carbomer (Carbopol 980, Lubrizol Advanced Materials, Inc.) | 1.0 |

(Production Method)

The components (1), (2), (3), and (4) were mixed and homogenized by stirring at 90° C. After that, the component (5) was added and homogeneously dispersed at 90° C. After the confirmation of the dissolution of the component (5), the solution was cooled to room temperature to afford a moisturizing oil gel.

The invention claimed is:

1. A method for producing an oily gel composition comprising
   mixing components (A), (B), and (C):
   (A) 4 to 60% by weight of a sphingosine of formula (1):

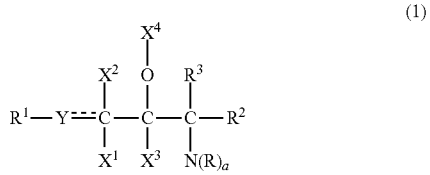

wherein
   $R^1$ represents a linear, branched, or cyclic, saturated or unsaturated hydrocarbon group having 4 to 30 carbon atoms which is optionally substituted by a hydroxyl group, a carbonyl group, or an amino group;
   Y represents a methylene group, a methine group, or an oxygen atom;
   each of $X^1$, $X^2$, and $X^3$ independently represents a hydrogen atom, a hydroxyl group, or an acetoxy group, and $X^4$ represents a hydrogen atom, an acetyl group, or a glyceryl group or forms an oxo group together with the adjacent oxygen atom, provided that, when Y represents a methine group, any one of $X^1$ and $X^2$ represents a hydrogen atom and the other is not present, and when $X^4$ forms an oxo group, $X^3$ is not present;
   each of $R^2$ and $R^3$ independently represents a hydrogen atom, a hydroxyl group, a hydroxymethyl group, or an acetoxymethyl group;
   each R independently represents a hydrogen atom or an amidino group or represent a linear or branched, saturated or unsaturated hydrocarbon group having a total of 1 to 8 carbon atoms which optionally have a substituent selected from the group consisting of a hydroxyl group, a hydroxyalkoxy group, an alkoxy group, and an acetoxy group;
   a represents a number of 2 or 3; and a bond represented by a broken line and a solid line indicates a saturated bond or an unsaturated bond;
   (B) 0.5 to 10% by weight of a water-soluble anionic polymer having a carboxyl group; and
   (C) 30 to 95.5% by weight of an oil in a liquid state at 25° C. selected from the group consisting of a hydrocarbon oil, an ester oil, and an ether oil
   to form a mixture; and
   heating the mixture to a temperature equal to or more than a melting point of the component (A) to neutralize the component (B) with the component (A) to form a salt, the heated mixture containing no more than 0.5%, including 0%, by weight of water,
   wherein component (C) is present in a continuous oil phase.

2. The method for producing an oily gel composition according to claim 1, wherein a weight ratio, (A)/(B), of component (A) to component (B) is 5 to 30.

3. The method for producing an oily gel composition according to claim 1, wherein component (B) is an anionic polymer comprising a monomer obtained from acrylic acid or methacrylic acid.

4. The method for producing an oily gel composition according to claim 1, wherein said mixing comprises mixing components (A) and (B), heating the mixture to a temperature equal to or more than the melting point of component (A) to neutralize the component (B) with component (A) to form a salt, and then mixing the salt with component (C).

5. The method for producing an oily gel composition according to claim 1, wherein said mixing comprises melting component (A) by heating to a temperature equal to or more than the melting point of component (A) thereby obtaining a melt, mixing and dissolving the melt in component (C) heated to a temperature equal to or more than the melting point of component (A), and then adding the component (B) to the solution to neutralize component (A) to form a salt.

6. The method for producing an oily gel composition according to claim 1, wherein component (A) is at least one member selected from the group consisting of
   a natural type sphingosine of formula (2):

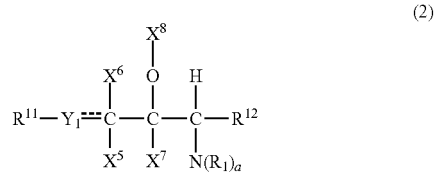

wherein
   $R^{11}$ represents a linear, branched, or cyclic, saturated or unsaturated hydrocarbon group having 7 to 19 carbon atoms which is optionally substituted by a hydroxyl group; $Y_1$ represents a methylene group or a methine group;
   each of $X^5$, $X^6$, and $X^7$ independently represents a hydrogen atom, a hydroxyl group, or an acetoxy group, and $X^8$ represents a hydrogen atom or forms an oxo group together with the adjacent oxygen atom, provided that, when $Y_1$ represents a methine group, any one of $X^5$ and $X^6$ represents a hydrogen atom and the other is not present, and when $X^8$ forms an oxo group, $X^7$ is not present;
   $R^{12}$ represents a hydroxymethyl group or an acetoxymethyl group;
   each $R_1$ independently represents a hydrogen atom or an amidino group or represent a linear or branched, saturated or unsaturated hydrocarbon group having a total of 1 to 4 carbon atoms which optionally have a substituent selected from the group consisting of a hydroxyl group, a hydroxyalkoxy group, an alkoxy group, and an acetoxy group;
   a represents a number of 2 or 3; and a bond represented by a broken line and a solid line indicates a saturated bond or an unsaturated bond, and
   a pseudo type sphingosine of formula (3):

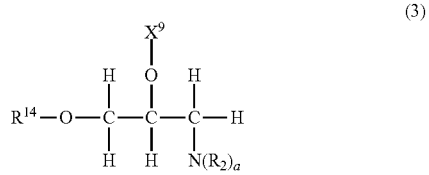

wherein
- $R^{14}$ represents a linear, branched, or cyclic, saturated or unsaturated hydrocarbon group having 10 to 22 carbon atoms which is optionally substituted by a hydroxyl group;
- $X^9$ represents a hydrogen atom, an acetyl group, or a glyceryl group; and
- each $R_2$ independently represents a hydrogen atom or an amidino group or represent a linear or branched, saturated or unsaturated hydrocarbon group having a total of 1 to 8 carbon atoms which optionally have a substituent selected from the group consisting of a hydroxyl group, a hydroxyalkoxy group, an alkoxy group, and an acetoxy group, and
- a represents a number of 2 or 3.

7. The method for producing an oily gel composition according to claim 1, wherein component (B) is at least one member selected from the group consisting of a polyacrylic acid, a polymethacrylic acid, an acrylic acid-alkyl methacrylate copolymer, an acrylate/$C_{10-30}$ alkyl acrylate crosspolymer, and a carboxyvinyl polymer.

8. The method for producing an oily gel composition according to claim 1, wherein component (C) is at least one member selected from the group consisting of liquid paraffin, liquid isoparaffin, hydrogenated polyisobutene, squalane, n-octane, n-heptane, cyclohexane, cetyl isobutyl ether, dioctyl ether, ethylene glycol monolauryl ether, ethylene glycol dioctyl ether, and glycerol monooleyl ether.

9. The method for producing an oily gel composition according to claim 1, wherein component (A) is present in the composition in an amount of from 9 to 30% by weight of the composition.

10. The method for producing an oily gel composition according to claim 1, wherein component (B) is present in the composition in an amount of from 1 to 7% by weight of the composition.

11. The method for producing an oily gel composition according to claim 1, wherein component (C) is present in the composition in an amount of from 70 to 90.5% by weight of the composition.

12. The method for producing an oily gel composition according to claim 1, wherein the weight ratio of component (A) to component (B), (A)/(B), is 5 to 12.

* * * * *